(12) United States Patent
Schulhof

(10) Patent No.: US 8,728,054 B2
(45) Date of Patent: May 20, 2014

(54) SYRINGE-CARPULE ASSEMBLY

(75) Inventor: Steven Schulhof, Teaneck, NJ (US)

(73) Assignee: Synchrojet LLC, Teaneck, NJ (US)

( * ) Notice: Subject to any disclaimer, the term of this patent is extended or adjusted under 35 U.S.C. 154(b) by 692 days.

(21) Appl. No.: 12/607,498

(22) Filed: Oct. 28, 2009

(65) Prior Publication Data

US 2010/0106139 A1     Apr. 29, 2010

Related U.S. Application Data

(60) Provisional application No. 61/193,110, filed on Oct. 29, 2008.

(51) Int. Cl.
*A61M 31/00* (2006.01)

(52) U.S. Cl.
USPC ........... 604/518; 604/82; 604/85; 604/87; 604/89; 604/90; 604/91; 604/263

(58) Field of Classification Search
USPC ........... 604/82, 85, 87, 89–91, 191, 263, 184
See application file for complete search history.

(56) References Cited

U.S. PATENT DOCUMENTS

| | | | | |
|---|---|---|---|---|
| 3,367,746 A | * | 2/1968 | Maurukas | 422/510 |
| 4,031,892 A | | 6/1977 | Hurschman | |
| 4,413,991 A | * | 11/1983 | Schmitz et al. | 604/191 |
| 4,755,169 A | * | 7/1988 | Sarnoff et al. | 604/511 |
| 4,873,193 A | * | 10/1989 | Jensen et al. | 436/176 |
| 5,037,402 A | | 8/1991 | Bartman | |
| 5,171,220 A | | 12/1992 | Morimoto | |
| 5,286,257 A | | 2/1994 | Fischer | |
| 5,330,426 A | * | 7/1994 | Kriesel et al. | 604/89 |
| 5,338,311 A | * | 8/1994 | Mahurkar | 604/195 |
| 5,364,369 A | | 11/1994 | Reynolds | |
| 5,429,610 A | | 7/1995 | Vaillancourt | |
| 5,476,449 A | | 12/1995 | Richmond | |
| 5,496,284 A | | 3/1996 | Waldenburg | |
| 5,580,786 A | | 12/1996 | Gombrich et al. | |
| 5,665,068 A | | 9/1997 | Takamura | |
| 5,685,846 A | | 11/1997 | Michaels, Jr. | |
| 5,788,670 A | | 8/1998 | Reinhard et al. | |
| 5,971,953 A | | 10/1999 | Bachynsky | |
| 6,132,400 A | | 10/2000 | Waldenburg | |
| 6,468,250 B2 | | 10/2002 | Yang | |
| 6,692,468 B1 | | 2/2004 | Waldenburg | |
| 6,972,005 B2 | | 12/2005 | Boehm, Jr. et al. | |
| 2005/0245880 A1 | | 11/2005 | Howlett et al. | |
| 2006/0178644 A1 | | 8/2006 | Reynolds | |

* cited by examiner

*Primary Examiner* — Kevin C Sirmons
*Assistant Examiner* — Edelmira Bosques
(74) *Attorney, Agent, or Firm* — Ostrager Chong Flaherty & Broitman P.C.

(57) ABSTRACT

A syringe-carpule assembly comprising first and second carpules, a housing holding the first and second carpules in an end-to-end relationship, an outer hollow plunger rod supported by and slidable relative to the housing, and an inner hollow rod having first and second openings and being slidably arranged inside the outer hollow plunger rod. The inner hollow rod is slidable between first and second positions. The inner hollow rod in the first position has the first opening disposed within the first carpule and the second opening disposed within the second carpule. This allows liquid solvent in the second carpule to flow into the first carpule, which comprises an evacuated chamber containing solid matter that dissolves in the presence of that solvent to form a mixture. The second carpule is then removed and the mixture in the first carpule is injected into the patient.

14 Claims, 4 Drawing Sheets

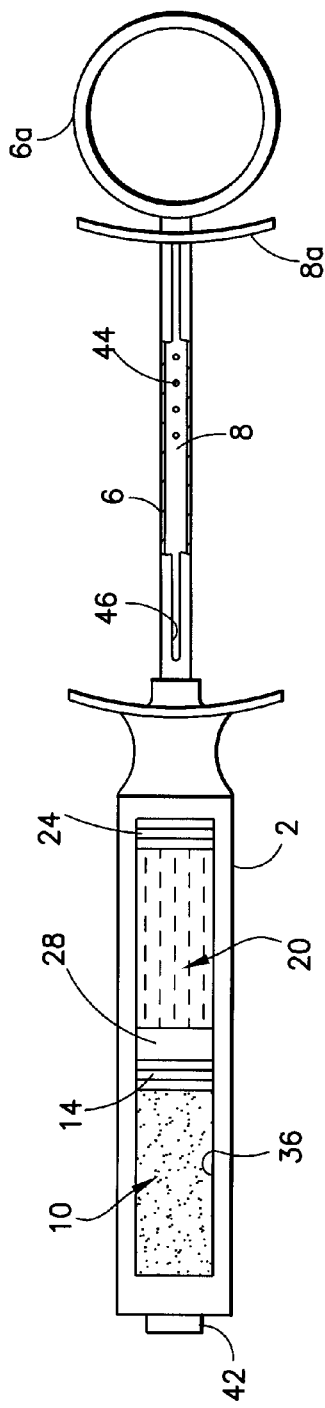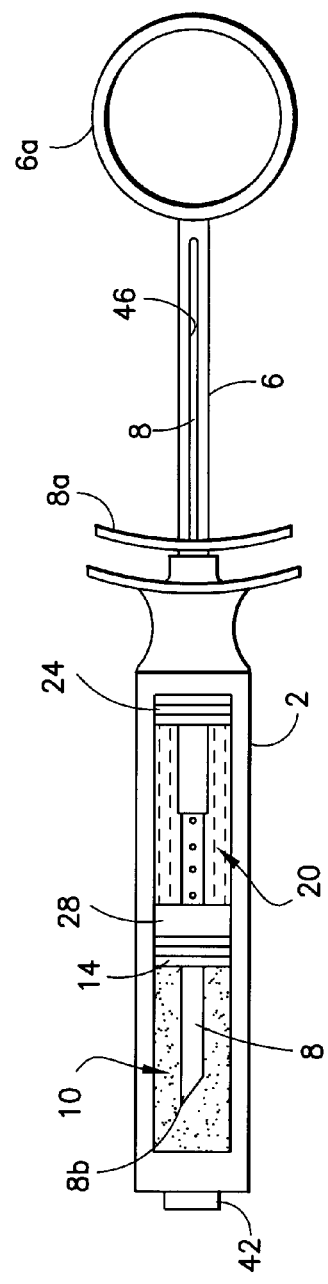
FIG. 4
FIG. 5

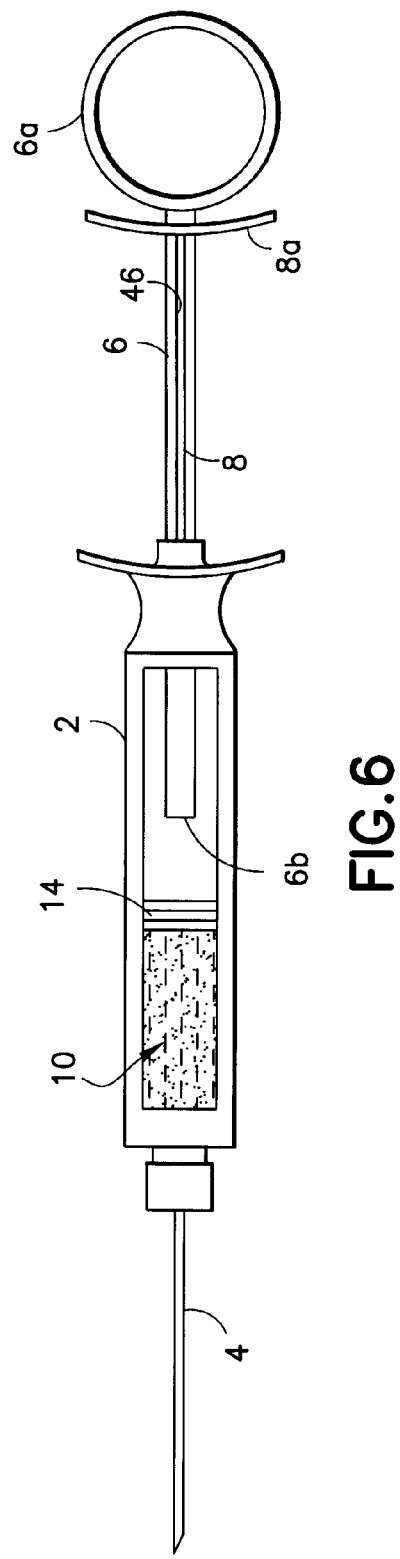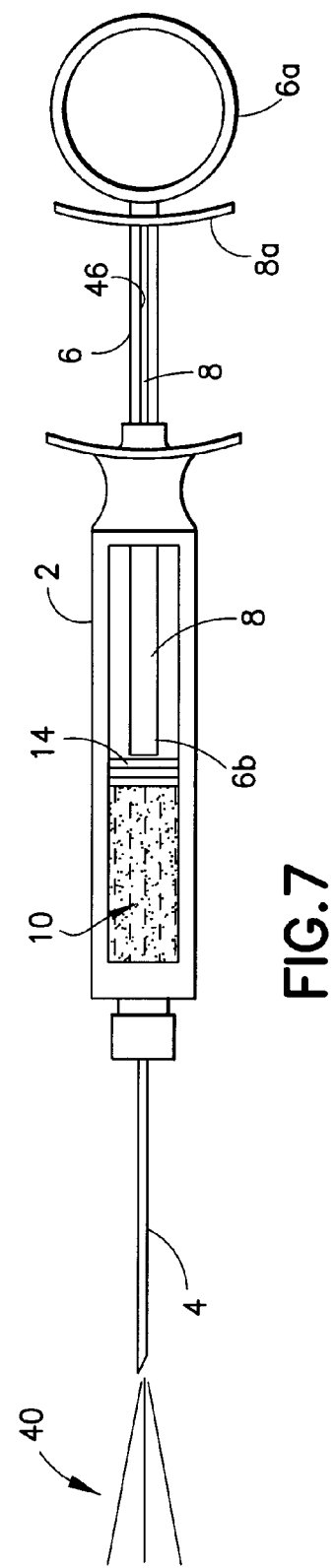

SYRINGE-CARPULE ASSEMBLY

RELATED PATENT APPLICATION

This application claims the benefit, under Title 35, United States Code, §119(e), of U.S. Provisional Application No. 61/193,110 filed on Oct. 29, 2008.

BACKGROUND

This invention generally relates to multi-chamber syringes for use in delivering drugs to medical patients. In particular, this invention relates to dual-chamber syringes that allow solid medicine (such as lyophilized material or powder) and liquid solvent (such as water or saline) to be pre-mixed prior to injection into a patient.

Conventionally powdered medicine, liquid solvents and injection device are normally used when powdered injection medicines are given. The powdered medicines are filled aseptically into a vial or an ampule container (referred to as a "carpule" hereinafter). As liquid solvents, distilled water for injection or an isotonic sodium chloride solution are filled aseptically in an ampule or carpule. Typically a syringe is used as the injection device.

It is known in the prior art to provide a syringe having two chambers: one filled with the solid medicine and the other filled with liquid solvent. The solid and liquid are pre-mixed before injection into a human body.

There is a need for an improved system to enable the delivery of drugs that come in two forms (i.e. lyophilized matter or powder and liquid solvent) that need to be premixed in an easy, single use, such as when injecting botulinum toxin. Preferably the improved system is sterilizable, uses disposable carpules, and allows blood to be aspirated to alert the operator that he/she is mistakenly in a blood vessel.

BRIEF SUMMARY

The present invention is directed to a system and a method for injecting medicine into a patient. The system is a syringe-carpule assembly comprising first and second carpules, a housing holding the first and second carpules in an end-to-end relationship, an outer hollow plunger rod supported by and slidable relative to the housing, and an inner perforated hollow rod slidably arranged inside the outer hollow plunger rod. The inner perforated hollow rod is slidable between first and second positions. The inner perforated hollow rod in the first position has at least one perforation disposed within the first carpule and at least one perforation disposed in the second carpule. This allows liquid solvent in the second carpule to flow into the first carpule, which comprises an evacuated chamber containing solid matter that dissolves in the presence of that solvent to form a mixture. The second carpule is then removed and the mixture in the first carpule is injected into the patient.

More specifically, one aspect of the invention is a syringe comprising a housing capable of holding first and second carpules, an outer hollow plunger rod supported by and slidable relative to the housing, and an inner hollow rod slidably arranged inside said outer hollow plunger rod. The inner hollow rod has first and second openings and is slidable between first and second positions. The inner hollow rod in the first position has the first opening disposed within the first carpule and the second opening disposed within the second carpule when the first and second carpules are held within the housing with the first carpule in front of the second carpule.

Another aspect of the invention is a syringe-carpule assembly comprising first and second carpules, a housing capable of holding the first and second carpules such that the first carpule is forward of the second carpule, an outer hollow plunger rod supported by and slidable relative to the housing, and an inner hollow rod slidably arranged inside the outer hollow plunger rod. The inner hollow rod is slidable between first and second positions. The inner hollow rod in the first position has a first opening disposed within the first carpule and a second opening disposed within the second carpule.

A further aspect of the invention is a method of administering a medicine to a medical patient using a syringe, comprising the following steps: (a) placing a first carpule containing solid matter in a chamber and a second carpule containing liquid solvent in a chamber inside a housing of a syringe in an end-to-end relationship with the first carpule in front of the second carpule, the chamber of the first carpule having an internal pressure less than atmospheric pressure; (b) placing a hollow rod of the syringe so that a first opening thereof is located inside the chamber of the first carpule and a second opening thereof is located inside the chamber of the second carpule, thereby causing liquid solvent to flow through the hollow rod and into the chamber of the first carpule, where the liquid solvent dissolves the solid matter to form a mixture; (c) removing the hollow rod from the chambers of the first and second carpules; (d) attaching a needle to the syringe housing; (e) removing the second carpule from the syringe housing; and (f) forcing at least a portion of the mixture to flow from the chamber of the first carpule into and through the needle.

Other aspects of the invention are disclosed and claimed below.

BRIEF DESCRIPTION OF THE DRAWINGS

FIG. 1 is a drawing showing two carpules respectively containing botulinum toxin and saline in accordance with one embodiment of the invention.

FIG. 2 is a drawing showing a rectangular piece of adhesive tape that is wrapped around respective portions of the carpules depicted in FIG. 1 to couple those carpules together in end-to-end relationship.

FIG. 4 is a drawing showing portions of a syringe-carpule assembly in accordance with one embodiment of the invention, which assembly includes the coupled carpules depicted in FIG. 2. The device is shown in a state wherein botulinum toxin in the forward carpule and saline solution in the rearward carpule have not yet been mixed and a needle has not yet been screwed onto the syringe housing.

FIG. 5 is a drawing showing the same assembly depicted in FIG. 4, with the difference that an inner perforated hollow rod has been advanced to a position whereat the saline solution in the rearward carpule is drawn into the forward carpule.

FIG. 6 is a drawing showing the syringe-carpule assembly after the botulinum toxin and saline solution have been mixed in the forward carpule (shown in FIG. 5), the rearward carpule has been removed and a needle has been screwed onto the syringe housing.

FIG. 7 is a drawing showing the same assembly depicted in FIG. 6 as the mixture in the forward carpule is being injected into a medical patient (not shown).

Reference will hereinafter be made to the drawings in which similar elements in different drawings bear the same reference numerals.

DETAILED DESCRIPTION

Figure 3:
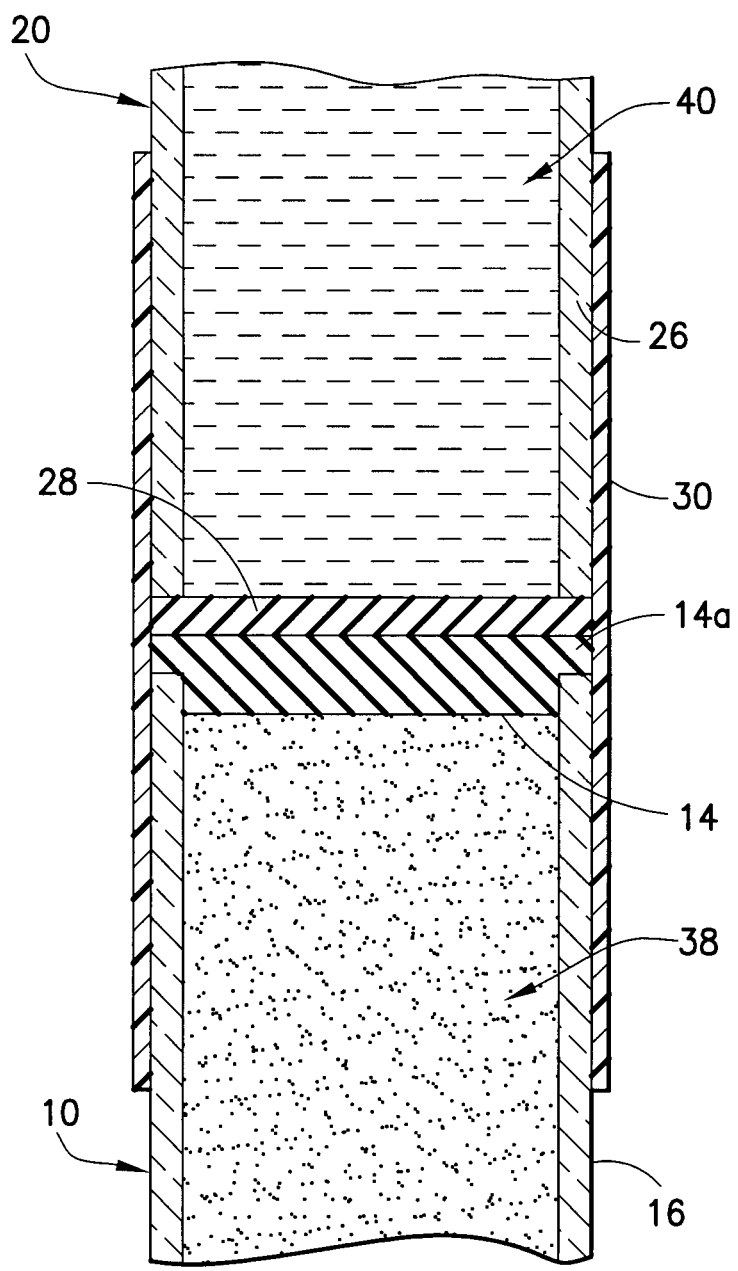
FIG. 3 is a sectional view showing respective portions of the coupled carpules depicted in FIG. 2.

A method of administering a medicine to a medical patient using a syringe in accordance with one embodiment of the invention will now be described. Two carpules are arranged end-to-end and then inserted into a syringe. The first carpule has an evacuated chamber containing lyophilized matter or powder; the second carpule contains liquid solvent.

Figures 1, 2:
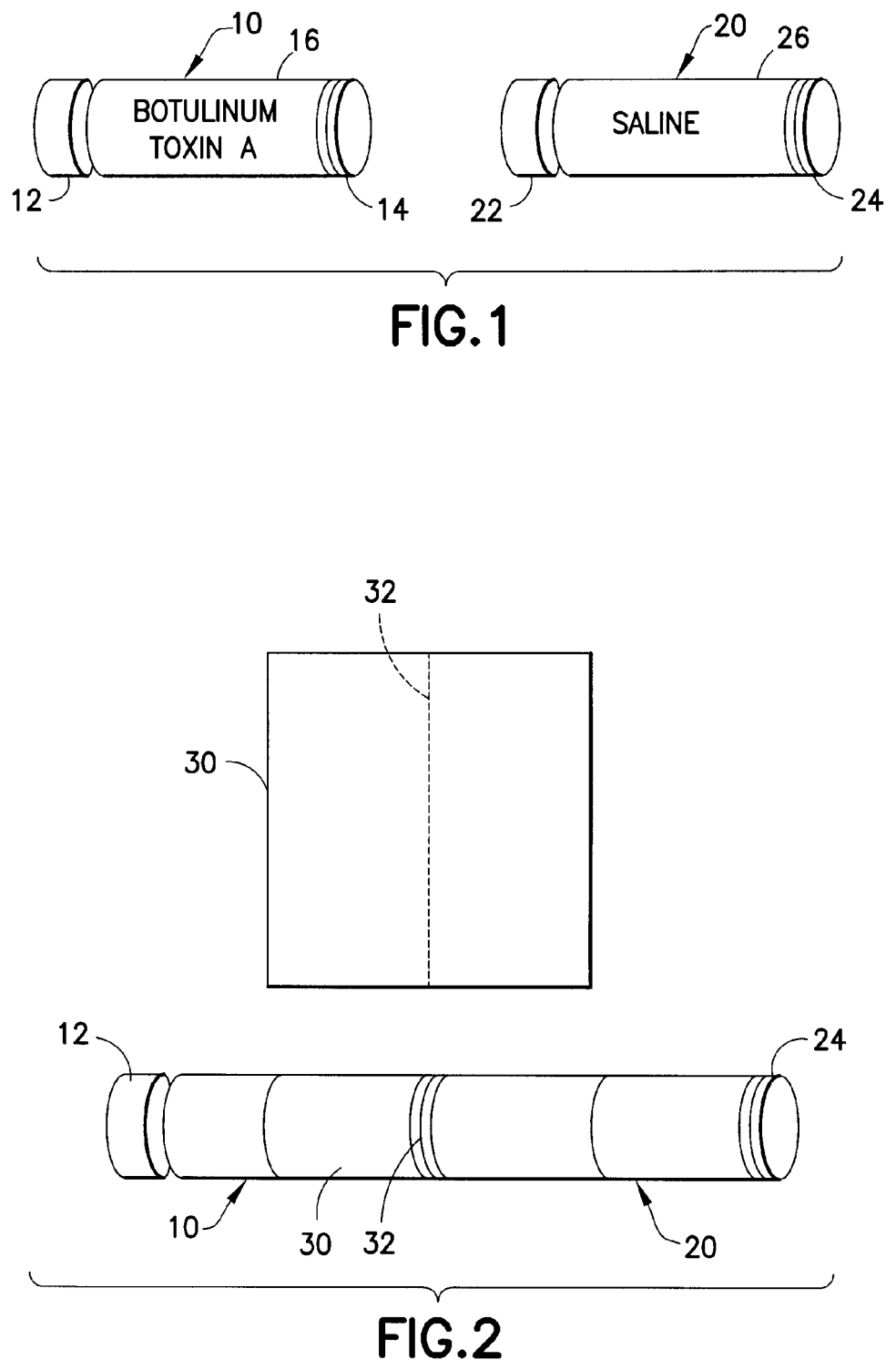

In the example disclosed hereinafter, the first carpule 10 (see FIG. 1) contains botulinum toxin while the second carpule 20 contains saline. Carpule 10 comprises a generally cylindrical glass vial 16 with openings at both ends. The forward end of vial 16 is covered by a rubber membrane (not shown in FIG. 1) that is held in place by a cap 12 made of metal foil. Although not shown in FIG. 1, it is known that the cap 12 has a circular opening (not shown) at its center that exposes a portion of the aforementioned rubber membrane. The rearward end of vial 10 is closed by a rubber stopper 14. Carpule 20 comprises a generally cylindrical glass vial 26 with openings at both ends. The forward end of vial 26 is covered by a rubber membrane (not shown in FIG. 1) that is held in place by a cap 22 made of metal foil. Cap 22 also has a circular opening (not shown) at its center that exposes a portion of the rubber membrane. The rearward end of vial 26 is closed by a rubber stopper 24.

The carpules 10 and 20 depicted in FIG. 1 can be arranged so that their centerlines are collinear, with the cap 22 of carpule 20 abutting the rubber stopper 14 of carpule 10. To hold the carpules in this end-to-end relationship, a rectangular piece of adhesive tape 30 (or other flexible substrate) is wrapped around respective portions of carpules 10 and 20, as seen in FIG. 2. The tape piece 30 has a line 32 of weakened tear resistance (e.g., a row of small perforations spaced at regular intervals). The tape piece should be positioned such that when it is wrapped around the abutting carpules, the tear line 32 is disposed in a plane perpendicular to the axes of the carpules and is aligned with the interface between the abutting carpules. As will be explained later, the tear line 32 facilitates the separation of the coupled carpules at a later stage in the method for administering medicine disclosed herein.

FIG. 3 is a sectional view showing respective portions of the coupled carpules except that, for ease of illustration, the metal cap 22 of carpule 20 has been omitted. That metal cap, if shown in FIG. 3, would have a circumferential portion disposed between the vial 26 and the adhesive tape 30 and an annular portion disposed between the rubber stopper 14 of carpule 10 and the rubber membrane 28 of carpule 20. The rubber stopper 14 includes a portion disposed within the vial 16 and a flange portion 14*a* that is trapped between the rear end surface of vial 16 and the front end of carpule 20. This arrangement serves to hold the rubber stopper 14 in position when it is penetrated by an inner perforated hollow rod of the syringe, as will described hereinafter with reference to FIGS. 5 and 7.

As seen in FIG. 3, carpule 10 contains lyophilized botulinum toxin 38 and carpule 20 contains saline solution 40. As is well known in the art, the lyophilized botulinum toxin must be dissolved in the saline solution before it can be injected into a patient. This is accomplished using the syringe depicted in FIG. 4.

FIG. 4 shows portions of a syringe-carpule assembly in accordance with one embodiment of the invention, which assembly includes the coupled carpules depicted in FIG. 2. The device is shown in a state wherein the lyophilized botulinum toxin in the forward carpule 10 and the saline solution in the rearward carpule 20 have not yet been mixed and a needle has not yet been screwed onto the syringe housing.

The syringe comprises a housing 2 capable of holding the coupled carpules 10 and 20 such that carpule 10 is in front of carpule 20, an outer hollow plunger rod 6 supported by and slidable relative to the housing 2, and an inner hollow rod 8 arranged inside the outer hollow plunger rod 6. The inner hollow rod 8 and the outer hollow plunger rod each comprise respective circular cylindrical tube portions, one slidable within the other. More specifically, the outer diameter of inner hollow rod 8 is slightly less than the inner diameter of outer hollow plunger rod 8, with sufficient clearance to allow the former to easily slide within the latter.

The housing 2 has a window 36 through which the coupled carpules can be inserted. A device, such as a swinging metal door (or other member) with a latch for locking it in a closed position, could be provided in the area of the front carpule 10 to hold it in place while the rear carpule 20 is being removed, as will be discussed later. The housing also has a threaded boss 42 to which a needle (item 4 in FIGS. 6 and 7) can be attached. The threaded boss 42 has a bore through which the rear end of the needle can penetrate the forward carpule 10 during needle attachment.

The inner hollow rod 8 is a circular cylindrical tube that is angled at its forward tip 8*b*. The space inside the hollow rod 8 forms a channel that ends as an opening in the angled forward tip 8*b*. The wall of the inner hollow rod is provided with a plurality of perforations or openings 44 arranged in two diametrally opposed rows (only one of these two rows is visible in FIGS. 4-6). The perforations 44 communicate with the open tip of inner hollow rod 8 via the channel therein. The inner hollow rod 8 is slidable between an extended position and a retracted position by the operator manipulating a handle 8*a* of the inner hollow rod 8. The handle 8*a* is slidable along the outside of the outer hollow plunger rod 6. The wall of the outer hollow plunger rod 6 has a longitudinal slot 46 that allows the handle 8*a* to be connected to the circular cylindrical wall of the inner hollow rod 8. This allows the inner hollow rod 8 to be slided by operation of handle 8*a*.

The inner hollow rod 8 is shown retracted in FIG. 4 and extended in FIG. 5. As seen in FIG. 4, in its retracted position the inner hollow rod 8 does not project into either carpule 10 or 20. As seen in FIG. 5, in its extended position inner hollow rod 8 projects through carpule 20 and the angled tip 8*b* of the inner hollow rod 8 projects into carpule 10. The angled or pointed tip 8*b* penetrates the rubber stopper 24 and rubber membrane 28 of carpule 20 and rubber stopper 14 of carpule 10. As is well known in the art, the rubber stoppers are provided with a pair of slits that intersect at right angles. The flexible rubber material adjacent these intersecting slits flexes apart during penetration of the pointed end 8*b* of inner hollow rod 8, allowing easy passage therethrough.

In the fully extended position of inner hollow rod 8, the opening at the angled tip 8*b* is disposed within carpule 10 and at least one and preferably more than one perforation 44 is disposed within carpule 20. Since inner rod 8 is hollow, in its fully extended position the inner hollow rod 8 provides a channel for flow communication between the internal chambers of carpules 10 and 20. Since the pressure inside the evacuated internal chamber of carpule 10 is lower than the pressure inside the liquid-filled carpule 20, the saline solution inside carpule 20 is drawn into carpule 10 by the pressure differential, flowing through the inner hollow rod 8.

After the saline solution has been drawn into the carpule 10, the syringe is then held upright in a vertical position as a needle 4 is screwed onto the threaded boss 42 of syringe housing 2, as seen in FIG. 6. During this procedure, the rear end of the needle penetrates the rubber membrane at the front of carpule 10. Then the inner hollow rod 8 is retracted, again by operator manipulation of the handle 8a. The substantially empty rear carpule 20 is then removed by tearing the adhesive tape 30 along its tear line 32. The saline solution now inside carpule 10 dissolves the lyophilized botulinum toxin. FIG. 6 shows the syringe with attached needle 4 and with the second carpule removed.

The outer hollow plunger rod 6 is slidable between retracted and extended positions relative to the syringe housing 2. The front end of outer hollow plunger rod 6 carries a head 6b (seen in FIGS. 6 and 7) having an opening that allows passage therethrough of the pointed tip 8b of inner hollow rod 8. The head 6b is disposed within carpule 10 (not shown in the drawings) when the outer hollow plunger rod 6 is in its fully extended position, and is not disposed within carpule 10 when the outer hollow plunger rod 6 is in its fully retracted position. The head 6b is preferably an annular ring that screws onto the end of the outer hollow plunger rod 6. The opening of that annular ring 6b allows the inner hollow rod 8 to pass through. The ring 6b can be unscrewed and removed to allow access to the inner hollow rod 8.

After the doctor inserts the needle 4 into the patient (not shown in FIG. 6), the doctor then injects the medicine into the patient. This is accomplished by the operator moving the outer hollow plunger rod 6 from its retracted position until head 6b engages the rubber stopper 14 (see FIG. 7). As the outer hollow plunger rod 6 is moved forward of its position depicted in FIG. 7, i.e., toward its fully extended position, by the operator, the flat annular head 6b of the advancing outer plunger rod 6 pushes the rubber stopper toward the front end of carpule 10. As the rubber stopper 14 moves forward, it forces the mixture 40 of dissolved botulinum toxin and saline solution through and out the needle 4, as seen in FIG. 7.

In accordance with an alternative embodiment, the head of the outer hollow plunger rod 6 can take the form of a harpoon or triangle. Such a head would be shaped and dimensioned such that as the head bears against the slits formed in rubber stopper 14, the detents or wings projecting on opposite sides of the triangular head (beyond the radius of the outer plunger rod) would engage the rubber stopper 14. The frictional forces would be such that the rubber stopper 14 would be effectively coupled to the triangular head, whether the outer hollow plunger rod 6 were being extended or retracted. This has the advantage that blood from the patient could be aspirated by pulling the rubber stopper 14 back a short distance.

The invention is not limited to use in medical procedures involving the injection of lyophilized botulinum toxin, but rather has wide application in any procedure involving the mixing of lyophilized matter or powder and a liquid solvent followed by injection of the mixture into a patient. The method of administering a medicine to a patient comprises the following steps. A first carpule containing lyophilized matter or powder and a second carpule containing liquid solvent are coupled in an end-to-end relationship by wrapping adhesive tape or some other suitable flexible substrate tightly around respective portions of the two carpules. The chamber of the first carpule has an internal pressure less than atmospheric pressure and less than the internal pressure of the second carpule. The coupled carpules are then placed inside a housing of a syringe with the first carpule in front of the second carpule. The operator then moves a hollow rod of the syringe forward to a position whereat a first opening is located inside the chamber of the first carpule and a second opening is located inside the chamber of the second carpule, thereby causing liquid solvent in the second carpule to flow through the inner hollow rod and into the first carpule, where the liquid solvent dissolves the lyophilized matter or powder to form a mixture. The operator then moves the inner hollow rod back to its fully retracted position whereat the distal section thereof no longer penetrates either carpule. The syringe is then turned to a vertical position with the front end of the syringe housing above the rear end of that housing. In this position, the operator screws a needle onto the front end of the syringe housing. The substantially empty second carpule is then removed from the syringe housing by tearing the adhesive tape along a line of weakened tear resistance. The operator then moves an outer hollow plunger rod forward until its head engages a rubber stopper at the rear of the first carpule now containing the mixture. As the operator continues to advance the outer hollow plunger rod, the rubber stopper is carried forward, forcing the mixture to flow from the first carpule into and through the needle. Upon injection, the operator places his thumb inside the aspirating ring 6a (see FIG. 7) at the rear of the outer hollow plunger rod and then pulls the ring rearward to aspirate.

The system disclosed herein enables the delivery of drugs that come in two forms (i.e. lyophilized matter or powder and liquid solvent) that need to be premixed in an easy, single use, such as when injecting botulinum toxin. Mixing of the two ingredients in a disposable vial sized to hold a single dosage avoids the waste that accompanies mixing larger volumes of ingredients in a bottle to produce a batch of doses that must be used within a fixed time frame. The present invention facilitates effective and cost efficient mixing of a single dosage of ingredients, thereby reducing the cost of drug application.

Another advantage is that the invention avoids human error in mixing the liquid and powder in the correct ratio. A further advantage lies in the fact the invention minimizes spill-off and residual medication in the multiple syringes that are used to draw up the medications in a multi-dose vial (each drop of medicine can be very expensive).

While the invention has been described with reference to various embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention.

The invention claimed is:

1. A syringe-carpule assembly comprising a housing, first and second carpules arranged inside said housing with said first carpule in front of said second carpule, an outer hollow plunger rod that passes through and is slidable in a rearward end of said housing, a first member connected to said outer hollow plunger rod and disposed outside said housing to the rear of said rearward end of said housing, an inner hollow rod comprising first and second openings disposed at different longitudinal positions, said inner hollow rod being slidably arranged inside said outer hollow plunger rod, and a second member connected to said inner hollow rod and disposed outside said housing to the rear of said rearward end of said housing, wherein said outer hollow plunger rod is slidable between a first extended position whereat said first member is disposed a first distance from said rearward end of said housing and a first retracted position whereat said first member is disposed a second distance from said rearward end of said housing, said second distance being greater than said first distance, and said inner hollow rod is slidable between a second extended position whereat said second member is disposed a third distance from said rearward end of said housing and a second retracted position whereat said second member is disposed a fourth distance from said rearward end of said housing, said fourth distance being greater than said third distance, and further wherein respective portions of said inner hollow rod are disposed inside said first and second carpules when said inner hollow rod is in said first extended position and outside said first and second carpules when said inner hollow rod is in said first retracted position.

2. The syringe-carpule assembly as recited in claim 1, wherein said first carpule has an evacuated chamber containing solid matter, and said second carpule has a chamber containing liquid solvent.

3. The syringe-carpule assembly as recited in claim 2, wherein said first carpule comprises a glass vial having open front and rear ends, a rubber membrane that closes said open front end of said first vial, and a rubber stopper that closes said open rear end of said first vial, said solid matter being contained inside said first vial between said rubber membrane and said rubber stopper.

4. The syringe-carpule assembly as recited in claim 3, wherein said rubber stopper comprises a flange that is sandwiched between said second carpule and said glass vial of said first carpule.

5. The syringe-carpule assembly as recited in claim 1, further comprising a flexible substrate wrapped around respective portions of said first and second carpules, said flexible substrate having a line of weakened tear resistance.

6. The syringe-carpule assembly as recited in claim 1, wherein said first member comprises an aspirating ring connected to a rearward end of said outer hollow plunger rod.

7. The syringe-carpule assembly as recited in claim 1, further comprising a head connected to a forward end of said outer hollow plunger rod, wherein said head is disposed within said first carpule when said outer hollow plunger rod is in said first extended third position, and said head is not disposed within said first carpule when said outer hollow plunger rod is in said first retracted position.

8. The syringe-carpule assembly as recited in claim 1, wherein said outer hollow plunger rod comprises a cylindrical wall with a longitudinal slot, and said second member comprises a handle connected to said inner hollow rod through said longitudinal slot, said handle being manually operable by an operator to slide said inner hollow rod forward relative to said outer hollow plunger rod.

9. A method of administering a medicine to a patient using a syringe, comprising the following steps:
   (a) placing a first carpule containing solid matter in a chamber and a second carpule containing liquid solvent in a chamber inside a housing of a syringe in an end-to-end relationship with said first carpule in front of said second carpule, said chamber of said first carpule having an internal pressure less than atmospheric pressure;
   (b) placing a hollow rod of said syringe so that a first opening thereof is located inside said chamber of said first carpule and a second opening thereof is located inside said chamber of said second carpule, thereby causing liquid solvent to flow through said hollow rod and into said chamber of said first carpule, where said liquid solvent dissolves said solid matter to form a mixture;
   (c) removing said hollow rod from said chambers of said first and second carpules;
   (d) attaching a needle to said syringe housing;
   (e) removing said second carpule from said syringe housing; and
   (f) forcing at least a portion of said mixture to flow from said chamber of said first carpule into and through said needle.

10. The method as recited in claim 9, wherein step (f) comprises the following steps:
   placing a head of a hollow plunger rod in contact with a rubber stopper disposed at a rear end of said first carpule; and
   using said hollow plunger rod to push said rubber stopper toward said needle at least until a portion of the mixture inside said first carpule has passed through and exited said needle.

11. The method as recited in claim 9, wherein step (b) comprises the following steps: piercing a rubber stopper disposed at a rear end of said second carpule, piercing a rubber membrane disposed at a front end of said second carpule, and piercing a rubber stopper disposed at a rear end of said first carpule.

12. The method as recited in claim 9, wherein said solid matter comprises botulinum toxin and said liquid solvent comprises saline.

13. The method as recited in claim 9, further comprising the following step performed prior to step (a): wrapping a flexible substrate around respective portions of said first and second carpules.

14. The method as recited in claim 13, wherein said flexible substrate has a line of weakened tear resistance, and step (e) comprises the step of tearing said flexible substrate along said line of weakened tear resistance.

* * * * *